United States Patent [19]
Charles et al.

[11] Patent Number: 5,176,628
[45] Date of Patent: Jan. 5, 1993

[54] VITREOUS CUTTER

[75] Inventors: Steven T. Charles, Germantown, Tenn.; Hugh J. Tyler, deceased, late of Santa Ana, by Barbara A. Tyler for the Hugh J. Tyler Family Trust; David M. Domash, Mission Viejo, both of Calif.

[73] Assignee: Alcon Surgical, Inc., Fort Worth, Tex.

[21] Appl. No.: 701,947

[22] Filed: May 16, 1991

Related U.S. Application Data

[63] Continuation-in-part of Ser. No. 427,880, Oct. 27, 1989, abandoned.

[51] Int. Cl.⁵ ............................................. A61B 17/32
[52] U.S. Cl. ........................................ 604/22; 606/171
[58] Field of Search ............ 606/170, 171, 180, 168; 604/22; 128/751, 752, 755

[56] References Cited

U.S. PATENT DOCUMENTS

| | | |
|---|---|---|
| 3,732,858 | 5/1973 | Banko . |
| 3,945,375 | 3/1976 | Banko . |
| 3,996,935 | 12/1976 | Banko . |
| 4,200,106 | 4/1980 | Douvas et al. . |
| 4,433,687 | 2/1984 | Burke et al. . |
| 4,436,091 | 3/1984 | Banko . |
| 4,516,575 | 5/1985 | Gerhard et al. . |
| 4,517,977 | 5/1985 | Frost . |
| 4,530,357 | 7/1985 | Pawloski et al. . |
| 4,577,629 | 3/1986 | Martinez . |
| 4,589,414 | 5/1986 | Yoshida et al. . |
| 4,603,694 | 8/1986 | Wheeler . |
| 4,662,869 | 5/1987 | Wright . |
| 4,674,502 | 6/1987 | Imonti . |
| 4,689,040 | 8/1987 | Thompson . |
| 4,696,298 | 9/1987 | Higgins et al. . |
| 4,735,605 | 4/1988 | Swartz . |
| 4,775,365 | 10/1988 | Swartz . |
| 4,792,327 | 12/1988 | Swartz . |
| 4,850,354 | 7/1989 | McGurk-Burleson et al. . |
| 4,867,155 | 9/1989 | Isaacson . |

OTHER PUBLICATIONS

Steve Charles, *Vitreous Microsurgery* (2nd ed. 1987), Chapter 2, pp. 25-41.

Primary Examiner—Michael H. Thaler
Attorney, Agent, or Firm—Jeffrey S. Schira

[57] ABSTRACT

An improved vitreous cutter having a housing with two halves connected together by tapered pins on one half fitting into holes on the other half with a proximal end, a distal end, an internal transverse bore and a longitudinal bore intersecting the transverse bore and penetrating the housing at the proximal and distal ends, a pair of inlets in the proximal end of the housing in fluid communication with opposite ends of the transverse bore for allowing pressurized air to be introduced into the transverse bore, a thermoplastic piston slideably received in the transverse bore having a toothed, longitudinal slot, a stainless steel stationary outer cutting tube having a cutting port on a distal end, a stainless steel rotatable inner cutting tube telescopically received in the outer cutting tube having a cutting port on a distal end and penetrating the proximal end of the housing to form a suction port, a flexible seal between the inner cutting tube and the outer cutting tube and a pinion gear on a medial section of the inner cutting tube that is received in the piston slot so as to rotate alternately the inner cutting tube within the outer cutting tube as the piston moves within the transverse bore in response to the pressurized air.

5 Claims, 5 Drawing Sheets

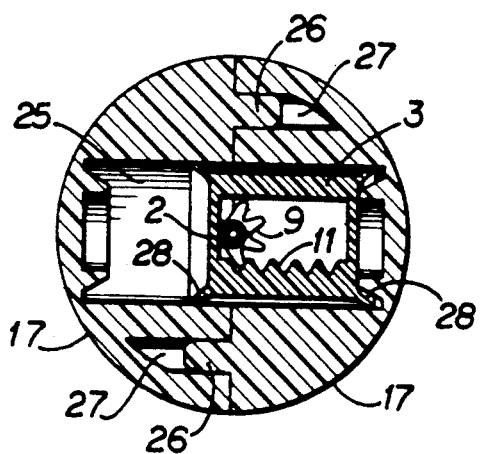
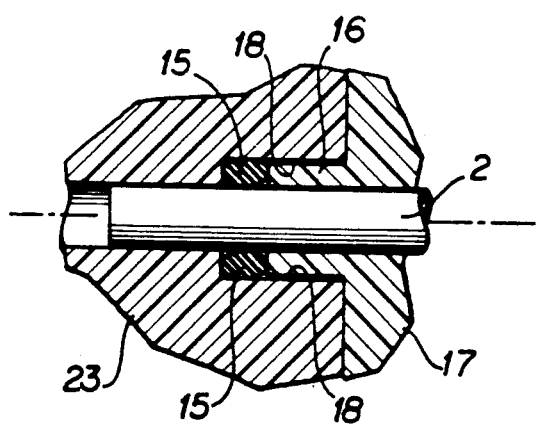
FIG 5  FIG 6
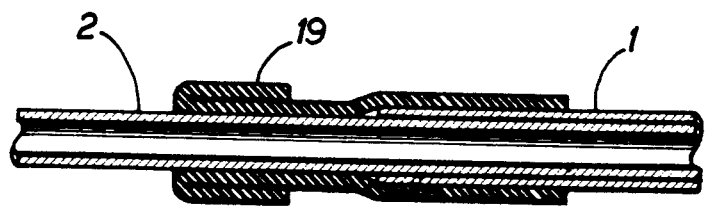
FIG 7
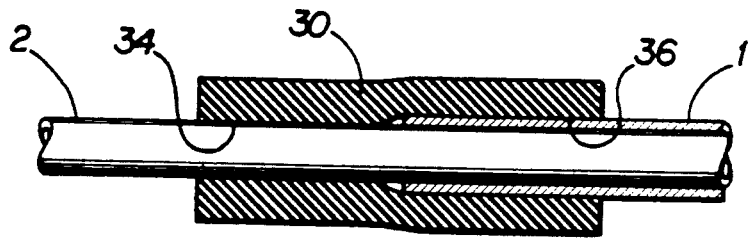
FIG 7A
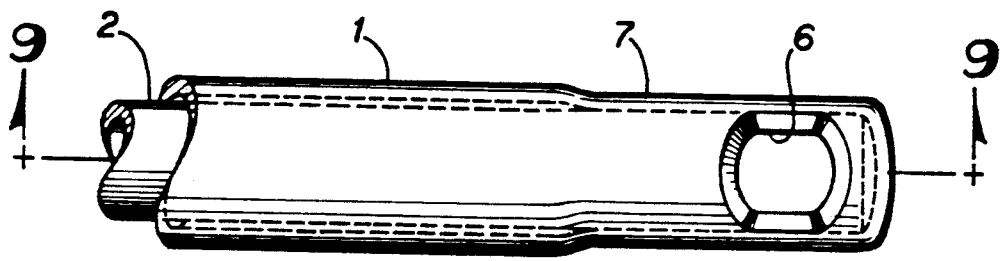
FIG 8

VITREOUS CUTTER

This application is a continuation-in-part application of U.S. patent application Ser. No. 07/427,880, filed Oct. 27, 1989, now abandoned.

BACKGROUND OF THE INVENTION

1. Field of the Invention

This invention relates generally to a surgical instrument and its assembly and more particularly concerns a surgical instrument used for removing vitreous from the eye during intraocular surgery.

2. Brief Description of the Prior Art

An eye surgery operation performed behind the lens is called vitreous surgery, inasmuch as the back part of the eye is filled with a clear material called vitreous. If the vitreous is damaged it must be completely removed before eye repairs can be made. When the vitreous is removed, the body quickly replaces it with a substitute clear liquid.

A surgical instrument used in vitreous surgery typically is a small, hand-held probe which is inserted into the eye through an incision, and which includes a tube which draws in the vitreous material, and a cutting means which severs the material, allowing it to be drawn out through the tube by suction.

Instruments now used in vitreous surgery generally consist of a concentric arrangement of an inner tube driven by an air powered diaphragm inside an outer tube, with the outer tube extending distally beyond the inner tube. The outer tube has a side facing opening adjacent to its distal tip. When suction is applied to the inner tube, the vitreous is moved into the side facing opening of the outer tube. When the inner tube is then pushed axially forward by the air powered diaphragm, it shears off the vitreous material projecting through the hole in the outer tube. The vitreous material is then aspirated through the inner tube by an external suction source.

This conventional construction has several disadvantages. The axial cutting motion of a diaphragm driven probe creates vibration in an axial direction due to the relatively large mass of the inner tube filled with liquid and the flexible suction tubing attached to the inner tube. This creates a danger of damage to the retina or other structures of the eye. The axial vibrations increase as practical cutting speed is approached because of the movement of the diaphragm and the inner tube.

Conventional air diaphragm driven vitreous cutter probes have other limitations as well. The cutting speed of such probes is limited by the axial vibration of the instrument. The power of the air driven diaphragm is also limited by the use of a return spring and the limited size of the diaphragm which is determined by the size of the instrument probe itself. The flexible tubing connected to the inner tube in the conventional air driven diaphragm construction of these surgical probes also tends to transmit dangerous vibrational motion to the instrument if the tubing is touched during the surgical procedure.

The general object of this invention is therefore to overcome these disadvantages and limitations by providing an improved vitreous cutting probe for use in removing vitreous from the eye during ophthalmic surgery.

A related object is to provide such a surgical probe which has relatively few parts, is simple in design, and is inexpensive to manufacture.

A more specific object of the invention is to overcome the safety and performance limitations of a probe employing the conventional axially-reciprocating, air-driven diaphragm vitreous cutter probes.

Another object of the current invention is to increase the cutting speed of the surgical probe.

A still further object of this invention is to provide a cutting device with an inner cutting needle capable of high precision cutting.

A related object is to simultaneously reduce vibration while increasing the cutting speed of the instrument.

It is a further object of the invention to provide a simple and effective means to isolate the moving inner tube from the external suction means and the stationary outer tube of the surgical probe.

Other objects and advantages of the present invention will be apparent to those skilled in this art from the following description and the appended claims.

SUMMARY OF THE INVENTION

The present invention is a surgical instrument, specifically a cutting probe. The instrument of the invention includes an outer tube having a proximal end and a closed distal end, and a side facing opening adjacent to the distal end. The side facing opening has a perimeter edge defining a cutting edge. The instrument also includes an inner tube housed within and concentric to the outer tube, and adapted to rotate relative to the outer tube. The inner tube has a proximal end and a distal end, and a segment of the inner tube extends proximally beyond the proximal end of the outer tube. The distal end of the inner tube is adjacent to the distal end of the outer tube, and the inner tube has a side facing opening adjacent to its distal end. The side facing opening of the inner tube has a perimeter edge defining a second cutting edge and it may be aligned with the side facing opening of the outer tube as the inner tube is rotated relative to the outer tube. A coupling means forms a seal between the inner and outer tubes, and it permits relative rotational movement between them. The instrument of the invention further includes a rotational means coupled to the inner tube to rotate the inner tube relative to the outer tube and a suction means coupled to the inner tube to draw material through to the interior of the inner tube when the inner tube is in a first rotational position, i.e., when the outer tube opening is aligned with the inner tube opening. When the inner tube is rotated to a second rotational position, i.e., where the opening of the inner tube is not aligned with the opening of the outer tube, the first cutting edge of the outer tube and the second cutting edge of the inner tube cooperate to sever a portion of the material present within the inner tube.

In one preferred embodiment, the rotation of the inner tube is achieved by a reciprocating piston having a rack that engages a pinion attached to the inner tube.

The preferred embodiments of the invention also employ a unitary elastomeric hose to couple the inner and outer tubes while allowing relative rotational movement between them.

The cutting probe of the invention also has an elongated, generally tubular housing which supports and substantially contains the inner and outer tubes and the rotational means. In the preferred embodiment, this housing consists of two identical halves. This preferred design allows for simple construction and easy manufacturing of the instrument since only a single mold is needed. Preferably, a lightweight plastic material is used to reduce cost and to permit production of disposable forms of the invention. The preferred configuration of the housing is a streamlined one, having a ribbed surface near the distal end to make the instrument more easily gripped and more easily maneuvered by the surgeon.

The cutting components of the instrument of the invention include an inner tube housed concentrically to an outer tube, both tubes having a proximal and a distal end, where each tube has a side facing opening adjacent to its distal end such that the inner tube may be rotated relative to the outer tube. The openings align at a first rotational position, and the perimeter edges of each opening cooperate to create a cutting action as the inner tube is rotated relative to the outer tube to a second rotational position.

In one preferred embodiment, the distal end of the outer tube is swaged slightly to produce an interference, or frictional, fit. In the preferred configuration, the open structure of the inner tube cutting edges allows these edges to be spring loaded against the outer tube, resulting in a self sharpening action of the inner cutting edges as they are rotated relative to the outer tube's inner surface. This preferred configuration further allows the cutting edges of the instrument to be close to its tip. This facilitates surgical manipulation, and allows the surgeon to get as close to the walls of the eye as possible.

These same advantages are achieved in an alternative preferred embodiment in which the cutting edge of the inner tube side opening is produced by grinding the inner tube to form a flat surface parallel to the axis of the tube. In this embodiment, the interference (or frictional) fit between the inner and outer tubes may be achieved without swaging the distal end of the outer tube. Rather, a deep slot is cut into the inner tube perpendicular to the axis of the inner tube and at the proximal edge of the inner tube side opening. The resulting inner tube wall segments are then forced outward so as to be slightly flared with respect to the remainder of the inner tube, thus permitting the cutting edges of the inner tube side opening to achieve an interference fit with the outer tube, while permitting the remainder of the inner tube to rotate within the outer tube without added frictional drag. This interference (or frictional) fit at the cutting tips of the inner and outer tubes provides maximum friction for a shearing or scissor-like cut, which is localized at the cutting tips, and it prevents vitreous material from entering the space between the outer and inner cutting tubes. This arrangement has the effect of spring loading the flat cut inner tube cutting edges against the outer tube allowing for more accurate cutting. As a further result of this arrangement, cutting occurs as close as possible to the distal end of the probe.

The rotational means employed in the preferred embodiments of the invention generally comprises a reciprocating air driven piston having in its interior a rack which engages a pinion attached to the inner tube. The piston preferably has air pressure seals at both ends. These seals create friction with the walls of the housing that prevents movement of the piston until there is sufficient air pressure buildup to snap the piston rapidly to its other limit, thereby increasing the cutting speed of the instrument.

Most preferedly, the piston and air pressure seals are manufactured from a single piece of material which is capable of forming both a thin stable sealing surface (the air pressure seals) and strong thick sections (the piston with internal rack) in one molding. This construction simplifies manufacturing and assembly of the invention. One material found suitable for manufacturing the piston of the present invention is a thermoplastic polyester elastomer such as that sold under the name HYTREL by E. I. duPont de Nemours and Co.

There are several advantages of the particular construction of preferred embodiment.

The low mass of the moving parts minimizes vibration of the surgical instrument. Also, because of the rotational cutting action of the invention, there are no dangerous in and out vibrations (as with prior diaphragm driven vitreous cutter probes), thus reducing the likelihood of unintentional damage to the retina when the instrument is used near the back wall of the eye. Additionally, the rotational cutting motion used in the invention does not produce an uncontrollable pumping action which limited the cutting speed of previous diaphragm driven vitreous cutters, because in the present invention, there is no axial movement between the inner and outer tubes which can cause fluid to oscillate inside the inner tube of the instrument. Another advantage of the preferred embodiment is that air pressure is used to positively drive the piston in both directions. This arrangement doubles the power output and significantly increases the cutting speed of the instrument because the piston does not have to work against a spring.

The preferred embodiment of the invention employs an external air pressure means which includes two separate air pressure sources connected to the instrument through the two outer ports on the end cap of the housing unit. Pressurized air entering each port is directed to one end of the chamber (formed in the housing) within which the piston reciprocates. In the preferred embodiment, the end cap not only creates an air pressure seal with the chamber which houses the reciprocating piston, but it also holds together two identical halves of the housing unit. The two external sources alternately supply air pressure to each of the outer ports to produce the reciprocating action of the piston.

The invention employs a coupling means which forms a seal between the inner and outer tubes while permitting relative rotational movement between the two tubes. In the preferred embodiment, this is accomplished by using a length of elastomeric hose having an internal diameter slightly smaller than the outer tube and slightly larger than the inner tube. The distal end of the hose fits snugly over the proximal end of the outer tube holding it securely in place. The proximal end of the inner tube extends beyond the proximal end of the outer tube and the proximal end of the hose. The proximal end of the hose is then folded distally over onto itself, thereby forming a double layer of hose in engagement with a portion of the inner tube. Alternately, this coupling member may be a molded unitary elastomeric member having two ends with different internal diameters to accommodate the inner and outer tubes.

These embodiments of the coupling means do not permit relative movement between either the inner or the outer tube at the proximal or distal end, respectively, of the elastomeric hose. The position of each tube with respect to the hose is fixed. Relative rotational movement between the inner and outer tube is, however, allowed because the center of the elastomeric hose is flexible and it twists as the inner tube is rotated. This preferred embodiment of the coupling means is simple and cost effective to manufacture. Moreover, since rotation of the inner tube is limited to a rather small arc by the rack and pinion driving mechanism, the elastomeric hose is subject to relatively little stress as a result of the twisting motion.

A suction means, such as a vacuum source, is coupled to the inner tube of the invention to draw the vitreous material into the interior of the inner tube so that a portion can be cut off and removed by suction through the tube. In the preferred embodiment, this suction means is not connected directly to the rotating inner tube, but is attached instead to the end cap of the housing. This construction creates less vibration in the suction tube which could be transmitted to the surgeon's hand, thus adding to the stability of the instrument during use.

The overall design of the preferred embodiment of the invention uses a minimum number of parts. This design simplicity allows for easy manufacturing, and the use of inexpensive materials makes the instrument cost effective to make and use as a disposable item.

DESCRIPTION OF THE DRAWINGS

FIG. 5 is a sectional view of the apparatus of the invention taken along line 5—5 of FIG. 4.

FIG. 6 is a partial sectional view of the proximal end of the end cap and the inner tube.

FIG. 7 is a sectional view of the inner and outer tube in concentric configuration coupled by the elastomeric hose.

FIG. 7A is a sectional view of the inner and outer tube in concentric configuration coupled by a unitary coupling member.

FIG. 8 is a plan view of the distal end of the inner and outer tubes in concentric configuration.

It should also be understood that the drawings are not necessarily to scale and that the embodiments are sometimes illustrated by graphic symbols, phantom lines, diagrammatic representations and fragmentary views. In certain instances, details difficult to perceive may have been omitted. It should be understood, of course, that the invention is not necessarily limited to the particular embodiments illustrated herein.

DETAILED DESCRIPTION

Figure 1:
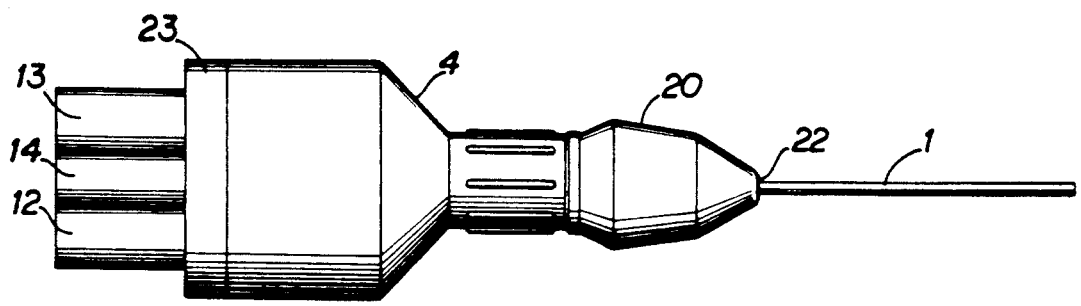
FIG. 1 is a plan view of an assembled vitreous cutter probe in accordance with the present invention.

A preferred embodiment of surgical instrument according to the present invention which provides a means for removing vitreous from the eye during ophthalmic surgery is shown assembled in the preferred embodiment in FIG. 1.

Figure 2:
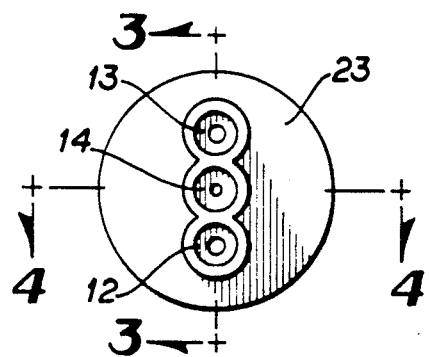
FIG. 2 is a plan view of the end cap.

The instrument includes as its basic components an outer tube 1, an inner tube 2, and a reciprocating air driven piston 3 (FIGS. 3–5), all partially encased by a housing 4. The housing 4 consists of more than one piece so that it may be easily assembled. Preferably, the housing 4 comprises two identical shells 17 (FIG. 3) with an annular nose piece 20 (FIGS. 1–3) on its distal end, and an end piece 23 (FIGS. 1–4) with two air supply fittings 12 and 13, and one suction port 14 at its proximal end. Each shell 17 is semicircular in cross section (see FIG. 5) so that when the two are assembled, they form the body of the elongated, generally tubular housing 4. The shells 17 are connected together by tapered pins 26 and holes 27, each shell having a single pin 26 and a single hole 27. The shells 17 are pressed together, forcing the pins 26 into the holes 27. The maximum diameter of the pins 26 is slightly larger than the diameter of the holes 27, causing an interference, or frictional, fit. The annular nose piece 20 slides over the distal tip portion of the concentric tubes 1 and 2 and snap fits into the circumferential retaining groove 21 at the distal end of the shells 17.

Figure 9:
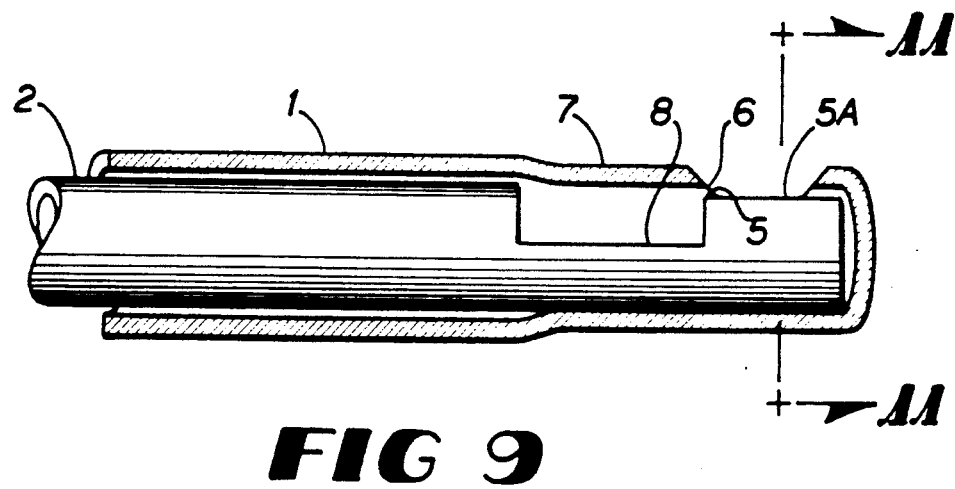
FIG. 9 is a partial sectional view of the distal end of the inner and outer tubes in concentric configuration in an open position where the inner tube opening is aligned with the outer tube opening.
Figure 10:
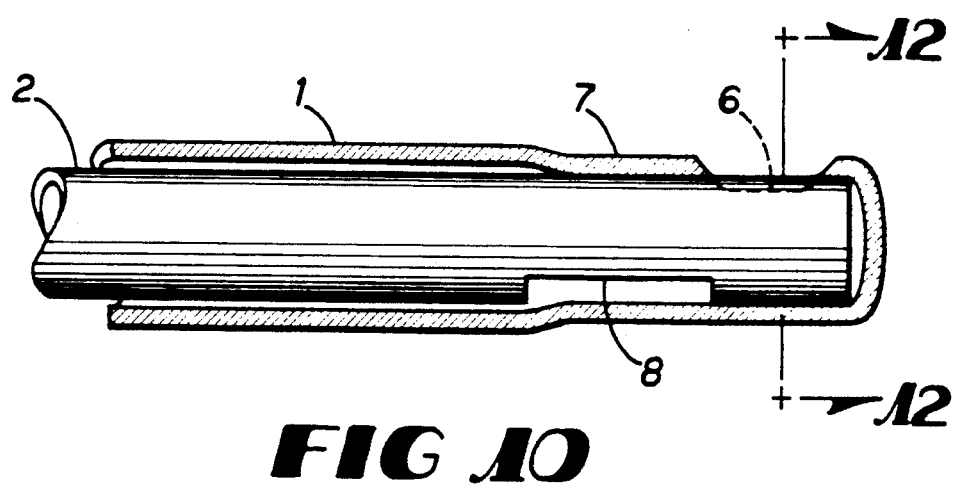
FIG. 10 is a partial sectional view of the distal end of the inner and outer tubes in concentric configuration in a closed position where the inner tube opening is not aligned with the outer tube opening.
Figure 11:
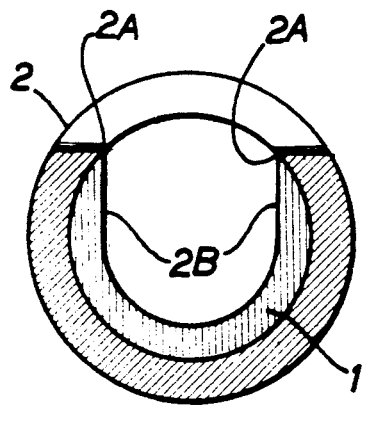
FIG. 11 is a sectional view of the distal end of the inner and outer tubes in concentric configuration in an open position where the inner tube opening is aligned with the outer tube opening taken along line 11—11 of FIG. 9.

The cutting action of the instrument in the first embodiment is effected by means of an edge 5 (FIGS. 9 and 10) (formed by cutting a slot 5 into the end of the inner tube 2), moving past an opening 6 cut in the outer tube 1. The inner cutting tube 2 and the outer cutting tube 1 frictionally engage each other, forming an interference fit at the cutting end. This interference fit accomplishes cutting by a shearing action, similar to that of a scissors, on account, in part, of friction between the inner tube cutting edge and the outer tube cutting edge. Additionally, this interference fit between the tubes prevents vitreous material from being pulled into the space between the inner and outer cutting tubes when the inner cutting tube 2 returns to its open position (FIG. 11). As shown in FIGS. 8-10, the distal end of the outer tube 1 has a swaged segment 7 to reduce as much as possible the space between the outer tube 1 and the inner tube 2, while still permitting relative rotation. A channel, or cross slot 8 is made in the inner tube 2, preferably by a saw cut perpendicular to the inner tube axis, so that only the cutting edge 5 makes a slight interference fit with the outer tube 1 in the swaged segment 7. This allows a self sharpening action of the cutting edge 5A, as well as confining the area of interference fit to the cutting ends of the outer tube 1 and the inner tube 2 so as to avoid a large increase in torque to drive the inner tube 2. This arrangement maximizes friction at the cutting end of the outer tube 1 and the inner tube 2 while minimizing friction between them elsewhere. Alternatively, the self sharpening action may be more economically achieved by simply lengthening the slot forming the cutting edge 5 so that its proximal edge extends proximally beyond swaged segment 7 of outer tube 1.

A material particularly well-suited for use in the cutter of the invention is stainless steel type 303, commonly known as hypodermic needle steel.

Figure 4:
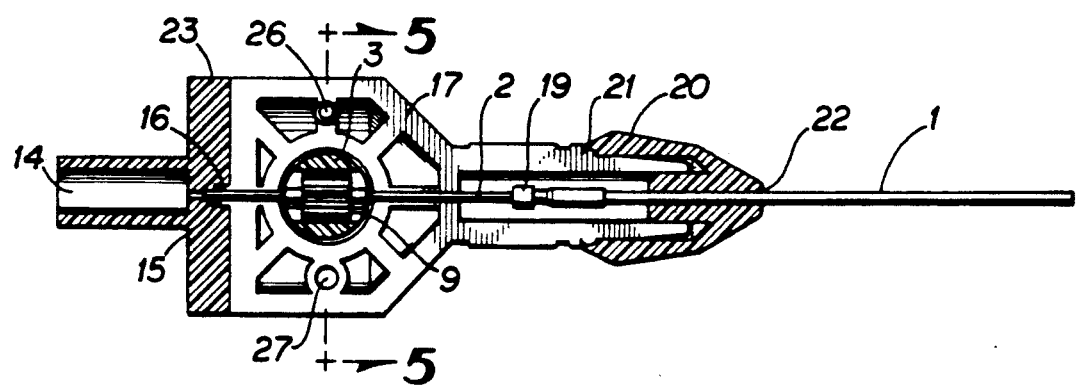
FIG. 4 is a sectional view of an assembled vitreous cutter taken along line 4—4 of FIG. 2.

Turning now to FIGS. 4 and 5, it can be seen that the inner tube 2 is driven by the pinion gear 9 fastened to the inner tube 2. The gear 9 engages rack 11 which is, in the preferred embodiment shown, integrally formed within piston 3. The piston 3 has a seal 28 at each end which contacts the wall of the chamber 25. In this preferred embodiment, the seals 28 are integrally formed within the piston 3. If air pressure is increased at fitting 12, the piston 3 will move up, rotating the gear 9 and the inner tube 2 attached to it to a closed position at which opening 5 is not aligned with opening 6 of outer tube 1 (FIG. 12), thereby cutting vitreous material which may have been aspirated into opening 6 of inner tube 2. Venting the pressure at fitting 12 and increasing the pressure at fitting 13 will move the piston down, rotating the gear 9 and the inner tube 2 attached to it to an open position shown in FIG. 11, ready to draw in new vitreous material to be cut.

Figure 12:
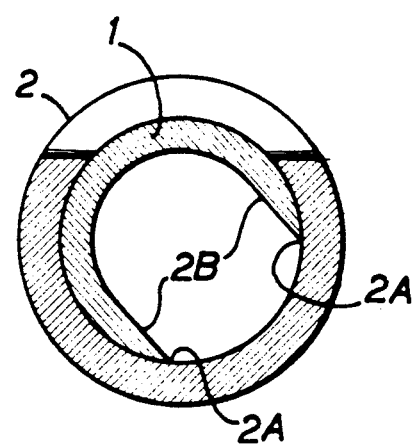
FIG. 12 is a sectional view of the distal end of the inner and outer tubes in concentric configuration in a closed position where the inner tube opening is not aligned with the outer tube opening taken along line 12—12 of FIG. 10.
Figure 13:
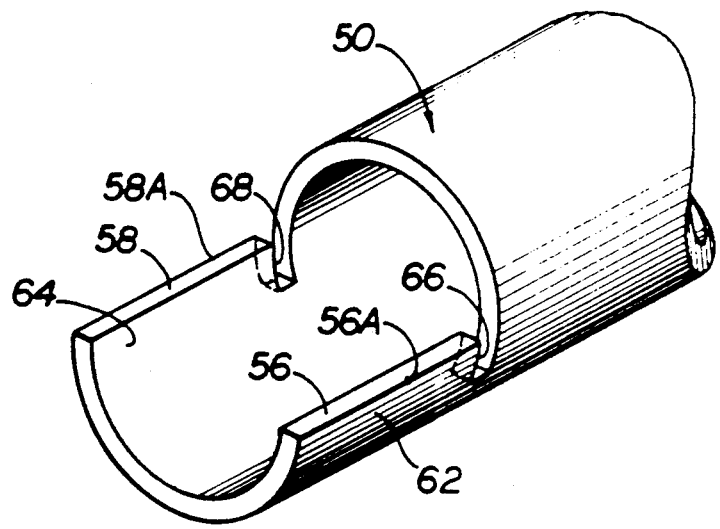
FIG. 13 is a perspective view of the inner cutting tube of a second embodiment having a slot cut across both sides of the inner tube at the proximal edge of the cutting opening and having a flared distal segment.
Figure 14:
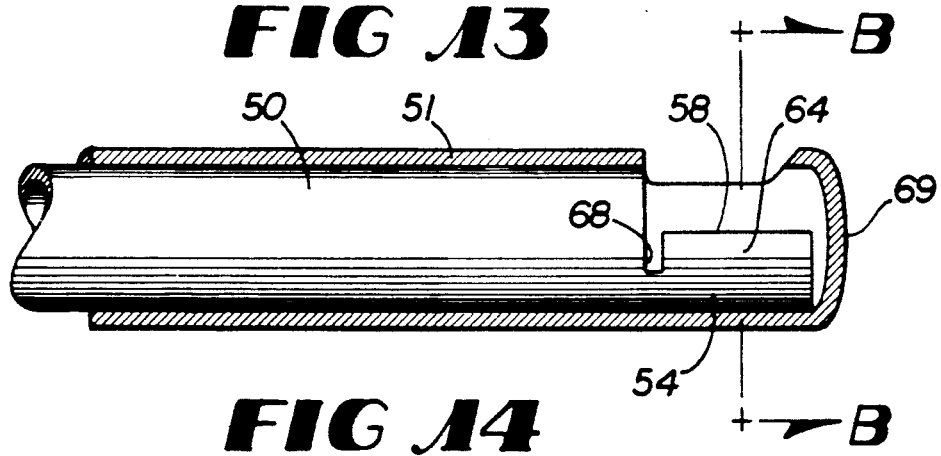
FIG. 14 is a partial sectional view of the distal end of the inner and outer tubes of the second embodiment wherein the inner tube opening is aligned with the outer tube opening.

With further respect to FIGS. 11 and 12, the inner cutting tube has a tapered edge 2a and square inner wall segments 2b. This inner cutting tube configuration is obtained by saw cutting a slot perpendicular to the axis of the tube into the distal end of the inner tube 2, using a blade having a thickness substantially equal to the internal diameter of the inner tube 2.

Suction applied to fitting 14 is connected to the inner needle 2 by means of an "O" ring 15, which is held in place by the semicircular projections 16 from the two body halves 17. The projections 16 also form a precision bearing for the inner tube 2 by being forced into precision bore 18 during assembly. This ensures that the projections 16 always are forced completely together in sealing engagement even though the two body halves 17 may be slightly apart due to slight imperfections in molding.

Figure 3:
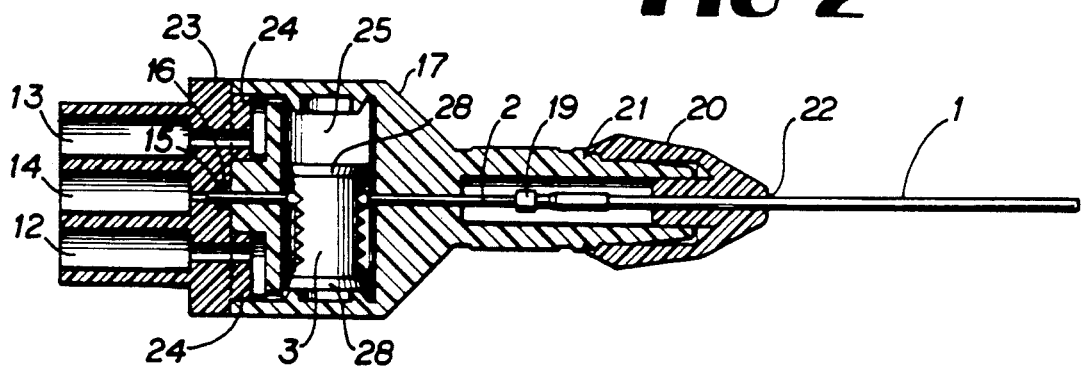
FIG. 3 is a sectional view of an assembled vitreous cutter taken along line 3—3 of FIG. 2.

Air leakage into the suction tube between the outer tube 1 and the inner tube 2 is prevented by seal 19 (FIGS. 3, 4, and 7). This seal 19 is made from an elastomeric hose having an internal diameter slightly smaller than the external diameter of outer tube 1 and larger than the external diameter inner tube 2. The proximal end of the hose is rolled back on itself to reduce its inner diameter of the tube so that it seals on the inner tube 2, but leaves a center section of the hose free to flex. This construction provides low torque and long life because there is no relative sliding.

FIG. 7A shows an alternative form of the seal 30 which is a unitary hose member molded from an elastomeric material such as silicone, a cross linked elastomer or other suitable polymer. In this embodiment, the seal 30 has two ends 34, 36, each with a different internal diameter. Both the larger and smaller internal diameter segments 34, 36, respectively, of the seal 30 are smaller before assembly than the outer diameters of the respective outer and inner tubes 1, 2. Thus, the smaller internal diameter segment 34 accommodates and forms a seal with the inner tube 2, while the larger internal diameter segment 36 accommodates and forms a seal with the outer tube 1. This configuration provides adequate sealing, while leaving the hose member 30 free to flex. This unitary hose construction is not only economical, but it is subject to only low torque, and therefore has long life because there is no relative sliding.

Assembly is accomplished as follows: A piston 3 is assembled into a first shell 17. The outer tube 1 is assembled to the inner tube 2, engaging seal 19. The inner and outer tube assembly, with gear 9 and seal 19 in place (see FIG. 4), is inserted in the piston opening so that the pinion gear 9 engages rack 11 (FIG. 5) and the second shell 17 is assembled to the first body half 17. The nose 20 is snapped into retaining groove 21 which is part of the body halves 17. The outer tube 1 is positioned so that the inner tube 2 is adjacent to the distal end of the outer tube 1 and the outer tube 1 is then bonded, e.g., by a drop of solvent, to the nose 20 at 22.

The end cap 23, containing fittings 12, 13, and 14, has two tapered projections 24 which include air connections leading from fitting 12 and 3 and which lie along an axis perpendicular to the inner and outer tube assembly and also perpendicular to the plane defined by the two shells. The projections 24 are spaced to pull the two body halves 17 together as well as make an air tight connection. The fittings 12 and 13 are offset on the projections 24, to bring the tubing connected to the fittings closer to the center line of the tool, thereby making the tool easier to control. Final adjustment is made by designating one fitting such as 13 as the cutter open position FIG. 11 and applying air pressure to move the piston 3 to the opposite end of the chamber 25, then the nose 20, which now has outer tube 1 bonded to it, is rotated until the cutter is fully open. Venting pressure at fitting 13 and applying pressure to fitting 12 will then close the cutter as in FIG. 12 by moving the piston 3 to the other end of the chamber 25.

The tool is fully operational at this time and can be tested. When proper performance is verified, end cap 23 and nose 20 can be permanently bonded to the body halves 17. If a defect is found during testing, the tool can be easily taken apart and repaired.

In addition to the embodiment described, there are additional embodiments within the scope of the present invention which employ inner tubes having their cutting edges formed in a different manner. These embodiments employ inner tubes having at least one outwardly flared perimeter edge. These additional inner tube configurations are illustrated in FIGS. 13-18.

Specifically turning to FIGS. 13, 14, 17, and 18 there is an inner cutting tube 50 within the outer cutting tube 51, containing an opening 52, with a cutting edge 52a. This outer cutting tube 51 is preferably of a uniform diameter, but it may be swaged. The distal cutting segment 54 of the inner cutting tube 50 has been ground parallel to the axis of the tube to produce two oppositely disposed flat surfaces 56, 58, with perimeter edges 56a, 58a. One perimeter edge 58a serves as a cutting edge. This distal cutting segment 54 of the inner tube 50 has a larger internal diameter than the remainder of the inner cutting tube 50, because its wall segments 62, 64 are flared outwardly. Downwardly extending slots 66, 68, are located at the proximal end of and on opposite sides 62, 64 of the distal cutting segment 54 of the inner cutting tube 50.

This alternate configuration is produced by grinding the distal cutting end of the inner cutting tube 50, to form a flat surface parallel to the axis of the inner tube, forming two flat surfaces 56, 58 on the wall segments 62, 64 of the inner tube. Slots 66, 68 are then cut at the proximal end of these surfaces. The wall segments 62, 64 of this ground inner tube end are then flared outwardly, preferably by axially pressing into the distal end of the inner tube 50 a needle or pin having an external diameter greater than the internal diameter of the inner tube. The resulting inner tube 50 includes a distal cutting segment 54 having a larger internal diameter than the remainder of the inner cutting tube 50.

Accordingly, this manufacturing process results in a device with an interference or friction fit between the inner cutting tube 50 and outer cutting tube 51 only at the cutting tip 69. Like the first preferred embodiment, this additional embodiment maximizes friction required for shearing at the cutting tip 69. Similarly, this alternate arrangement allows for a more accurate cut, since the cutting edge 58a is as close as possible to the outer tube opening 52. Since the outer cutting tube 51 frictionally engages the inner cutting tube 50 at the cutting tip 69, the possibility of tearing of vitreous which could have entered into the space between the inner and outer cutting tubes 50, 51, is minimized. Moreover, this manufacturing process is economical as it eliminates costly steps of swaging the outer cutting tube 1 and cutting a cross slot 8 in the inner cutting tube 2 (FIGS. 9 and 10).

Figure 15:
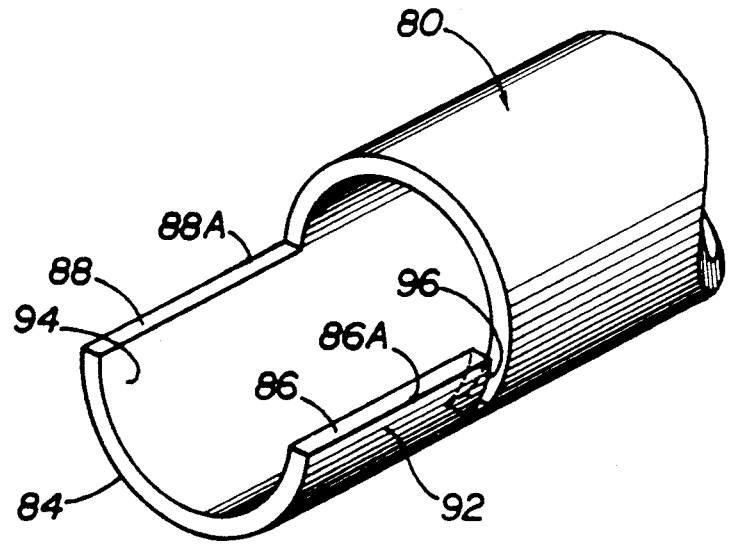
FIG. 15 is a perspective view of the inner cutting tube of a third embodiment having a slot cut on only one side of the tube at the proximal edge of the cutting opening and having a flared distal segment.
Figure 16:
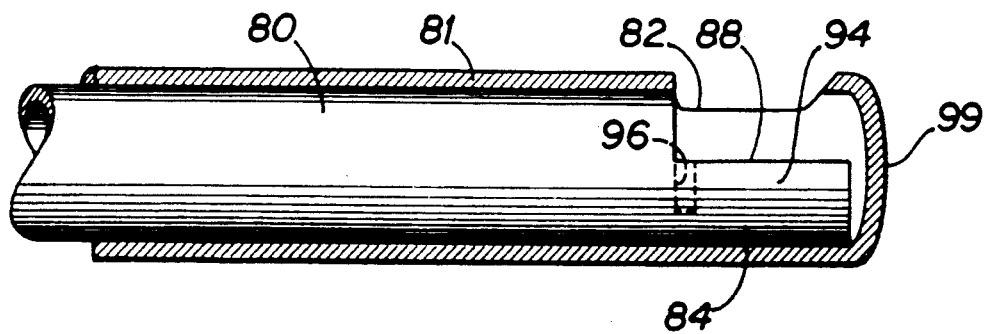
FIG. 16 is a partial sectional view of the distal end of the inner and outer tubes of the third embodiment in concentric configuration wherein the inner tube opening is aligned with the outer tube opening.
Figure 17:
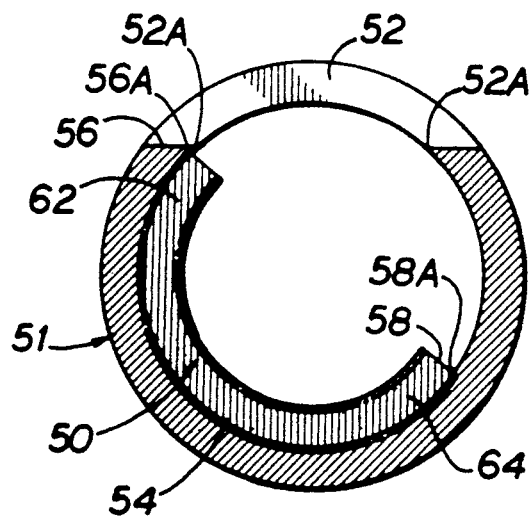
FIG. 17 is a sectional view of the distal end of the inner and outer tubes of the second embodiment in a position in which the inner tube opening is aligned with the outer tube opening, taken along line B—B of FIG. 14.
Figure 18:
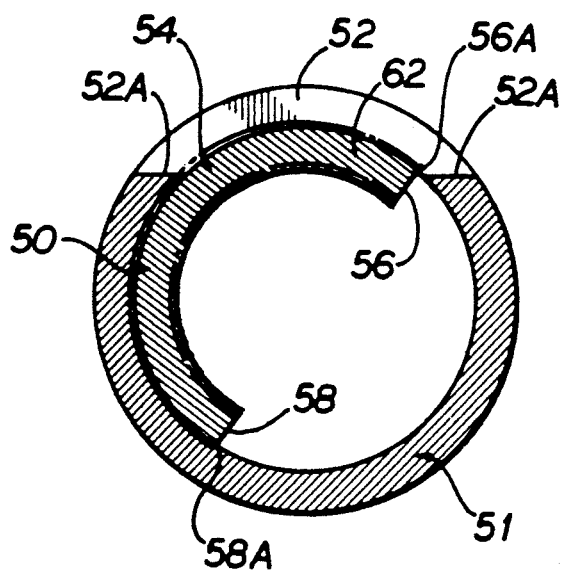
FIG. 18 is a sectional view of the distal end of the inner and outer tubes of the second embodiment in which the inner tube opening is not aligned with the outer tube opening taken along line B—B of FIG. 14.

FIGS. 15 and 16 show an inner cutting tube 80 within an outer cutting tube 81, which is preferably of a uniform diameter, but it may be swaged. The distal cutting end 84 of the inner cutting tube 80 has been ground to form a surface parallel to the axis of the tube to produce two oppositely disposed flat surfaces 86, 88 with perimeter edges 86a, 88a at the outer ends. One perimeter edge 88a serves as a cutting edge. The distal cutting segment 84 of the inner cutting tube 80 has a larger internal diameter than the remainder of the inner cutting tube 80, because one wall segment 92 has been flared outwardly. The opposite wall segment 94 retains its initial curvature. A downwardly extending slot 96, formed by a single cut is located at the proximal end of the flared out wall segment 92 of the distal cutting segment 84 of the inner cutting tube 80.

This alternate configuration is produced by essentially the same process disclosed for the inner cutting needle with a distal end having two flared wall segments, except that a slot is cut on only one side of the inner tube opening and only one wall segment of this distal inner tube end is flared.

Accordingly, this manufacturing process results in an interference or friction fit between the inner cutting tube 80, and outer cutting tube 81 only at the cutting tip 99. Like the preferred embodiment, the friction required for shearing is maximized at the cutting tip 99. Similarly, this alternate arrangement allows for a more accurate cut, since the cutting edge 88a will be as close as possible to the outer tube opening 82. Since the outer cutting tube 81 frictionally engages the inner cutting tube 80 at the cutting tip 99, the possibility of tearing of vitreous which could have entered into the space between the inner and outer cutting tubes 80, 81 is minimized. Moreover, this manufacturing process is economical as it eliminates costly steps of swaging the outer cutting tube 1 and cutting a cross slot 8 in the inner cutting tube 2 (FIGS. 9 and 10).

From the foregoing description and examples, it is apparent that the objects of the present invention have been achieved. While only certain embodiments have been set forth, alternative embodiments and various modifications will be apparent to those skilled in the art. These and other alternatives and modifications are considered equivalents and within the spirit and scope of the present invention.

What is claimed is:

1. An improved vitreous cutter, comprising:
   a. a housing having a proximal end, a distal end, and internal transverse bore and a longitudinal bore intersecting the transverse bore and penetrating the housing at the proximal and distal ends;
   b. a pair of inlets in the proximal end of the housing in fluid communication with opposite ends of the transverse bore for allowing pressurized air to be introduced into the transverse bore;
   c. a piston slideably received in the transverse bore having a toothed, longitudinal slot;
   d. a stationary outer cutting tube having a cutting port on a distal end;
   e. a rotatable inner cutting tube telescopically received in the outer cutting tube having a cutting port on a distal end and penetrating the proximal end of the housing to form a suction port;
   f. a flexible seal between the inner cutting tube and the outer cutting tube; and
   g. a pinion gear on a medial section of the inner cutting tube that is received in the piston slot so as to rotate alternately the inner cutting tube within the outer cutting tube as the piston moves within the transverse bore in response to the pressurized air.

2. The vitreous cutter of claim 1 wherein the outer cutting tube and the inner cutting tube comprise stainless steel.

3. The vitreous cutter of claim 1 wherein the housing comprises two halves connected together by tapered pins on one half fitting into holes on the other half.

4. The vitreous cutter of claim 1 wherein the piston comprises thermoplastic.

5. An improved vitreous cutter, comprising:
   a. a housing having two halves connected together by tapered pins on one half fitting into holes on the other half with a proximal end, a distal end, an internal transverse bore and a longitudinal bore intersecting the transverse bore and penetrating the housing at the proximal and distal ends;
   b. a pair of inlets in the proximal end of the housing in fluid communication with opposite ends of the transverse bore for allowing pressurized air to be introduced into the transverse bore;
   c. a thermoplastic piston slideably received in the transverse bore having a toothed, longitudinal slot;
   d. a stainless steel stationary outer cutting tube having a cutting port on a distal end;

e. a stainless steel rotatably inner cutting tube telescopically received in the outer cutting tube having a cutting port on a distal end and penetrating the proximal end of the housing to form a suction port;

f. a flexible seal between the inner cutting tube and the outer cutting tube; and a pinion gear on a medial section of the inner cutting tube that is received in the piston slot so as to rotate alternately the inner cutting tube within the outer cutting tube as the piston moves within the transverse bore in response to the pressurized air.

* * * * *